(12) United States Patent
Kaneko

(10) Patent No.: US 12,148,195 B2
(45) Date of Patent: Nov. 19, 2024

(54) OBJECT DETECTION DEVICE, OBJECT DETECTION METHOD, AND PROGRAM

(71) Applicant: FUJIFILM Corporation, Tokyo (JP)

(72) Inventor: Kenichiro Kaneko, Tokyo (JP)

(73) Assignee: FUJIFILM Corporation, Tokyo (JP)

(*) Notice: Subject to any disclaimer, the term of this patent is extended or adjusted under 35 U.S.C. 154(b) by 358 days.

(21) Appl. No.: 17/728,984

(22) Filed: Apr. 26, 2022

(65) Prior Publication Data

US 2022/0351494 A1 Nov. 3, 2022

Related U.S. Application Data

(63) Continuation of application No. PCT/JP2020/037903, filed on Oct. 6, 2020.

(30) Foreign Application Priority Data

Oct. 30, 2019 (JP) .................................. 2019-197614

(51) Int. Cl.
*G06V 10/75* (2022.01)
*A61B 6/00* (2024.01)
(Continued)

(52) U.S. Cl.
CPC .............. *G06V 10/759* (2022.01); *A61B 6/50* (2013.01); *A61B 6/5217* (2013.01);
(Continued)

(58) Field of Classification Search
None
See application file for complete search history.

(56) References Cited

U.S. PATENT DOCUMENTS

| 9,858,496 | B2 | 1/2018 | Sun et al. |
| 2011/0142308 | A1* | 6/2011 | Ishikawa .................... G06T 3/18 |
| | | | 382/128 |

(Continued)

FOREIGN PATENT DOCUMENTS

| CN | 109767448 A | * 5/2019 |
| CN | 110232410 A | * 9/2019 |

(Continued)

OTHER PUBLICATIONS

"International Search Report (Form PCT/ISA/210) of PCT/JP2020/037903," mailed on Nov. 17, 2020, with English translation thereof, pp. 1-6.

(Continued)

*Primary Examiner* — Mohammed Rachedine
(74) *Attorney, Agent, or Firm* — JCIPRNET

(57) ABSTRACT

An object detection device that detects a specific object included in an input image includes a first candidate region specifying unit that specifies a first candidate region in which an object candidate is included from a first input image obtained by imaging a subject in a first posture, a second candidate region specifying unit that specifies a second candidate region in which an object candidate is included from a second input image obtained by imaging the subject in a second posture different from the first posture, a deformation displacement field generation unit that generates a deformation displacement field between the first input image and the second input image, a coordinate transformation unit that transforms a coordinate of the second candidate region to a coordinate of the first posture based on the deformation displacement field, an association unit that associates the first candidate region with the transformed second candidate region that is close to the first candidate region, and a same object determination unit that determines that the object candidates included in the candidate regions associated with each other by the association unit are the same object and are the specific object.

12 Claims, 11 Drawing Sheets

(51) Int. Cl.
*A61B 6/03* (2006.01)
*A61B 6/50* (2024.01)
*G06T 7/00* (2017.01)
*G06V 10/77* (2022.01)
*G06V 10/82* (2022.01)
*G06V 20/70* (2022.01)

(52) U.S. Cl.
CPC ........ *G06V 10/7515* (2022.01); *G06V 10/753* (2022.01); *G06V 10/7715* (2022.01); *G06V 10/82* (2022.01); *G06V 2201/032* (2022.01)

(56) References Cited

U.S. PATENT DOCUMENTS

| | | | | |
|---|---|---|---|---|
| 2012/0230559 | A1* | 9/2012 | Itai | G06T 7/0012 382/128 |
| 2015/0104737 | A1* | 4/2015 | Fujimura | G03F 1/78 716/51 |
| 2016/0225145 | A1* | 8/2016 | Nagata | G06T 7/0012 |
| 2017/0206670 | A1 | 7/2017 | Miyasa et al. | |

FOREIGN PATENT DOCUMENTS

| | | | |
|---|---|---|---|
| JP | 2011123682 | 6/2011 | |
| JP | 2011206297 | 10/2011 | |
| JP | 2012187161 | 10/2012 | |
| JP | 2015100619 | 6/2015 | |
| JP | 2015130973 | 7/2015 | |
| JP | 2016143194 | 8/2016 | |
| JP | 2017080157 | 5/2017 | |
| JP | 2017127623 | 7/2017 | |
| JP | 2017156886 | 9/2017 | |
| KR | 2020070062 A * | 6/2020 | ......... A61B 1/00016 |

OTHER PUBLICATIONS

"Written Opinion of the International Searching Authority (Form PCT/ISA/237)" of PCT/JP2020/037903, mailed on Nov. 17, 2020, with English translation thereof, pp. 1-8.

"Office Action of Japan Counterpart Application" with English translation thereof, issued on Dec. 13, 2022, p. 1-p. 7.

* cited by examiner

OBJECT DETECTION DEVICE, OBJECT DETECTION METHOD, AND PROGRAM

CROSS-REFERENCE TO RELATED APPLICATION

This application is a continuation application of International Application No. PCT/JP2020/037903, filed Oct. 6, 2020, the disclosure of which is incorporated herein by reference in its entirety. Further, this application claims priority from Japanese Patent Application No. 2019-197614 filed on Oct. 30, 2019, the disclosure of which is incorporated herein by reference in its entirety.

BACKGROUND

1. Technical Field

The present disclosure relates to an object detection device, an object detection method, and a program.

2. Description of the Related Art

In recent years, with the progress of medical equipment, such as a computed tomography (CT) apparatus and a magnetic resonance imaging (MRI) apparatus, an image diagnosis using a high-resolution three-dimensional image is realized. Automatic extraction of a region including an organ, a lesion, or the like included in such an image is also performed (see, for example, JP2017-127623A and JP2017-80157A).

In addition, as a method of extracting the region from such an image, a method of using a discriminator that is trained through machine learning, such as deep learning, is proposed. In particular, Faster-RCNN (regions with CNN features) is known as a convolution neural network (CNN) used in the deep learning (see U.S. Pat. No. 9,858,496B).

SUMMARY

As one of CT examination, the large intestine CT examination is known as a new large intestine examination that does not use an endoscope. In the large intestine CT examination, as a lesion, for example, a polyp of colorectal cancer that can be observed as a convex part in a lumen of the large intestine is detected. In such large intestine CT examination, a patient as a subject is imaged in two postures, supine (supine position) and prone (prone position). The reason for imaging the patient in two postures is that there is a risk that water droplets or the like is falsely detected as the polyp in one posture.

JP2017-127623A and JP2017-80157A disclose that a diagnosis is made using two images captured in different postures, but the detection of a lesion region is individually performed in each image. Therefore, in the related art, the detection accuracy of the lesion region largely depends on the experience and ability of a doctor, and thus there is a possibility that the false detection occurs.

The technology of the present disclosure is to provide an object detection device, an object detection method, and a program having less false detection than the related art.

In order to achieve the above object, the present disclosure relates to an object detection device that detects a specific object included in an input image, the device comprising a first candidate region specifying unit that specifies a first candidate region in which an object candidate is included from a first input image obtained by imaging a subject in a first posture, a second candidate region specifying unit that specifies a second candidate region in which an object candidate is included from a second input image obtained by imaging the subject in a second posture different from the first posture, a deformation displacement field generation unit that generates a deformation displacement field between the first input image and the second input image, a coordinate transformation unit that transforms a coordinate of the second candidate region to a coordinate of the first posture based on the deformation displacement field, an association unit that associates the first candidate region with the transformed second candidate region that is close to the first candidate region, and a same object determination unit that determines that the object candidates included in the candidate regions associated with each other by the association unit are the same object and are the specific object.

It is preferable that the object detection device further comprise a first object determination unit that determines that the object candidate included in the first candidate region is the specific object, and a second object determination unit that determines that the object candidate included in the second candidate region is the specific object.

In this case, it is preferable that the first object determination unit determine that the object candidate included in the first candidate region is the specific object, and the second object determination unit determine that the object candidate included in the second candidate region is the specific object.

In addition, it is preferable that the same object determination unit generate a main score indicating certainty that the object candidates included in the candidate regions are the same object and are the specific object, the first object determination unit generate a first sub-score indicating certainty that the object candidate included in the first candidate region is the specific object, and the second object determination unit generate a second sub-score indicating certainty that the object candidate included in the second candidate region is the specific object.

In addition, it is preferable that the object detection device further comprise a detection unit that detects, as the specific object, an object candidate having the main score equal to or greater than a first threshold value, an object candidate having the first sub-score equal to or greater than a second threshold value, which is greater than the first threshold value, and an object candidate having the second sub-score equal to or greater than the second threshold value.

It is preferable that the first object determination unit correct the first candidate region, and the second object determination unit correct the second candidate region.

It is preferable that the object detection device further comprise a first convolution neural network that generates a first convolution feature map from the first input image, and a second convolution neural network that generates a second convolution feature map from the second input image, in which the first candidate region specifying unit specifies the first candidate region based on the first convolution feature map, and the second candidate region specifying unit specifies the second candidate region based on the second convolution feature map.

It is preferable that the deformation displacement field generation unit be a convolution neural network that generates the deformation displacement field from the first convolution feature map and the second convolution feature map.

It is preferable that one of a supine position and a prone position be the first posture, and the other of the supine position and the prone position be the second posture. It is preferable that the specific object be a polyp.

The present disclosure relates to an object detection method of detecting a specific object included in an input image, the method comprising a first candidate region specifying step of specifying a first candidate region in which an object candidate is included from a first input image obtained by imaging a subject in a first posture, a second candidate region specifying step of specifying a second candidate region in which an object candidate is included from a second input image obtained by imaging the subject in a second posture different from the first posture, a deformation displacement field generation step of generating a deformation displacement field between the first input image and the second input image, a coordinate transformation step of transforming a coordinate of the second candidate region to a coordinate of the first posture based on the deformation displacement field, an association step of associating the first candidate region with the transformed second candidate region that is close to the first candidate region, and a same object determination step of determining that the object candidates included in the candidate regions associated with each other by the association step are the same object and are the specific object.

The present disclosure relates to a program operating a computer as an object detection device that detects a specific object included in an input image, the program operating the computer as a first candidate region specifying unit that specifies a first candidate region in which an object candidate is included from a first input image obtained by imaging a subject in a first posture, a second candidate region specifying unit that specifies a second candidate region in which an object candidate is included from a second input image obtained by imaging the subject in a second posture different from the first posture, a deformation displacement field generation unit that generates a deformation displacement field between the first input image and the second input image, a coordinate transformation unit that transforms a coordinate of the second candidate region to a coordinate of the first posture based on the deformation displacement field, an association unit that associates the first candidate region with the transformed second candidate region that is close to the first candidate region, and a same object determination unit that determines that the object candidates included in the candidate regions associated with each other by the association unit are the same object and are the specific object.

According to the technology of the present disclosure, the false detection can be reduced as compared with the related art.

BRIEF DESCRIPTION OF THE DRAWINGS

Exemplary embodiments according to the technique of the present disclosure will be described in detail based on the following figures, wherein.

DETAILED DESCRIPTION

Figure 1:
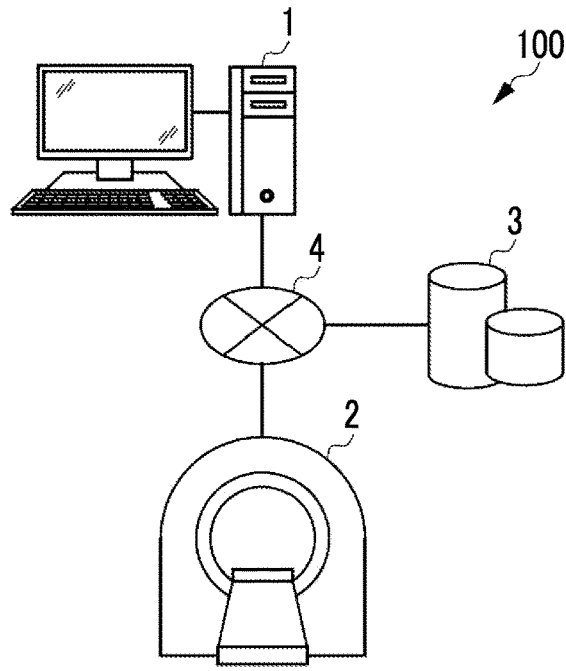
FIG. 1 is a hardware configuration diagram showing an outline of a diagnosis support system.

In the following, an embodiment of the present disclosure will be described with reference to the drawings. FIG. 1 is a hardware configuration diagram showing an outline of a diagnosis support system 100 to which an object detection device 1 according to the embodiment of the present disclosure is applied. As shown in FIG. 1, the diagnosis support system 100 includes an object detection device 1, a three-dimensional image capturing apparatus 2, and an image storage server 3. The object detection device 1, the three-dimensional image capturing apparatus 2, and the image storage server 3 are connected to each other via a network 4 in a communicable state.

The three-dimensional image capturing apparatus 2 is an apparatus that images a diagnosis target part of a subject to generate a three-dimensional image showing the part and is, specifically, a CT apparatus, an MRI apparatus, a positron emission tomography (PET) apparatus, and the like. The three-dimensional image generated by the three-dimensional image capturing apparatus 2 is transmitted to the image storage server 3 and stored therein. It should be noted that, in the present embodiment, the three-dimensional image capturing apparatus 2 is, for example, the CT apparatus, and a CT image including the diagnosis target part (for example, the abdomen of the human body) of the subject is generated as the three-dimensional image. It should be noted that the three-dimensional image is composed of a plurality of tomographic images.

The image storage server 3 is a computer which stores and manages various data, and includes a large-capacity external storage device and database management software. The image storage server 3 communicates with another apparatus via the wired or wireless network 4 to transmit and receive image data and the like between the other apparatus. Specifically, the image storage server 3 acquires various data including image data of the three-dimensional image generated by the three-dimensional image capturing apparatus 2 via the network 4, stores the acquired data in a recording medium, such as a large-capacity external storage device, and manages the data. It should be noted that a storage format of the image data and the communication between the apparatuses via the network 4 are based on a protocol, such as digital imaging and communication in medicine (DICOM).

The object detection device 1 is a computer on which an operation program is installed. The computer may be a workstation or a personal computer directly operated by a doctor who makes a diagnosis, or may be a server computer connected to the workstation or the personal computer via the network. The operation program is distributed by being recorded in a recording medium, such as a digital versatile disc (DVD) or a compact disc read only memory (CD-ROM), and is installed on the computer from the recording medium. Alternatively, the operation program is stored in a storage device of the server computer connected to the network or a network storage in a state of being accessible from the outside. In this case, the operation program is downloaded and installed on the computer used by the doctor in response to the request.

Figure 2:
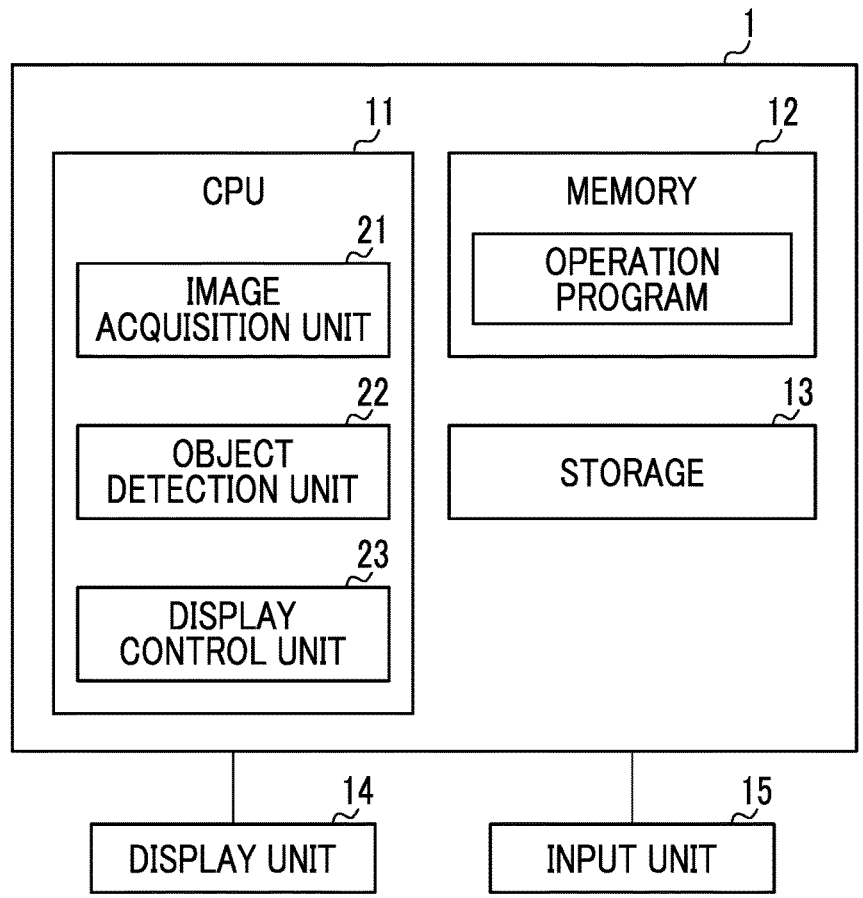
FIG. 2 is a diagram showing a schematic configuration of an object detection device.

FIG. 2 is a diagram showing a schematic configuration of the object detection device 1 realized by installing the operation program on the computer. As shown in FIG. 2, the object detection device 1 comprises, as a configuration of a standard workstation, a central processing unit (CPU) 11, a memory 12, and a storage 13. In addition, a display unit 14, such as a liquid crystal display, and an input unit 15, such as a keyboard and a mouse, are connected to the object detection device 1.

The storage 13 is composed of a hard disk drive or the like, and stores an input image acquired from the image storage server 3 via the network 4 and various information including information necessary for a process.

In addition, the operation program is stored in the memory 12. As a process to be executed by the CPU 11, the operation program defines an image acquisition process of acquiring the input image, which is a target of the object detection, an object detection process of detecting an object included in the input image, and a display control process of displaying the input image together with a detection result of the object. It should be noted that the input image may be the three-dimensional image or a two-dimensional image.

By the CPU 11 executing these processes according to the operation program, the CPU 11 functions as an image acquisition unit 21, an object detection unit 22, and a display control unit 23.

The image acquisition unit 21 is an interface that acquires the input image from the image storage server 3. It should be noted that, in a case in which the input image is already stored in the storage 13, the image acquisition unit 21 may acquire the input image from the storage 13.

In the present embodiment, the image acquisition unit 21 acquires two input images obtained by imaging the same subject under different imaging conditions. Specifically, the image acquisition unit 21 acquires two three-dimensional images obtained by imaging the subject in different postures by the three-dimensional image imaging apparatus 2 as a first input image S1 and a second input image S2. For example, the first input image S1 is a supine image obtained by imaging the subject in a state of lying on a bed (supine position), and the second input image S2 is a prone image obtained by imaging the subject in a state of lying face down on the bed (prone position).

The supine position is an example of a first posture, and the prone position is an example of a second posture. It should be noted that the first posture and the second posture are not limited to the supine position and the prone position, and need only be two different postures, such as a right lateral posture and a left lateral posture.

Figure 3:
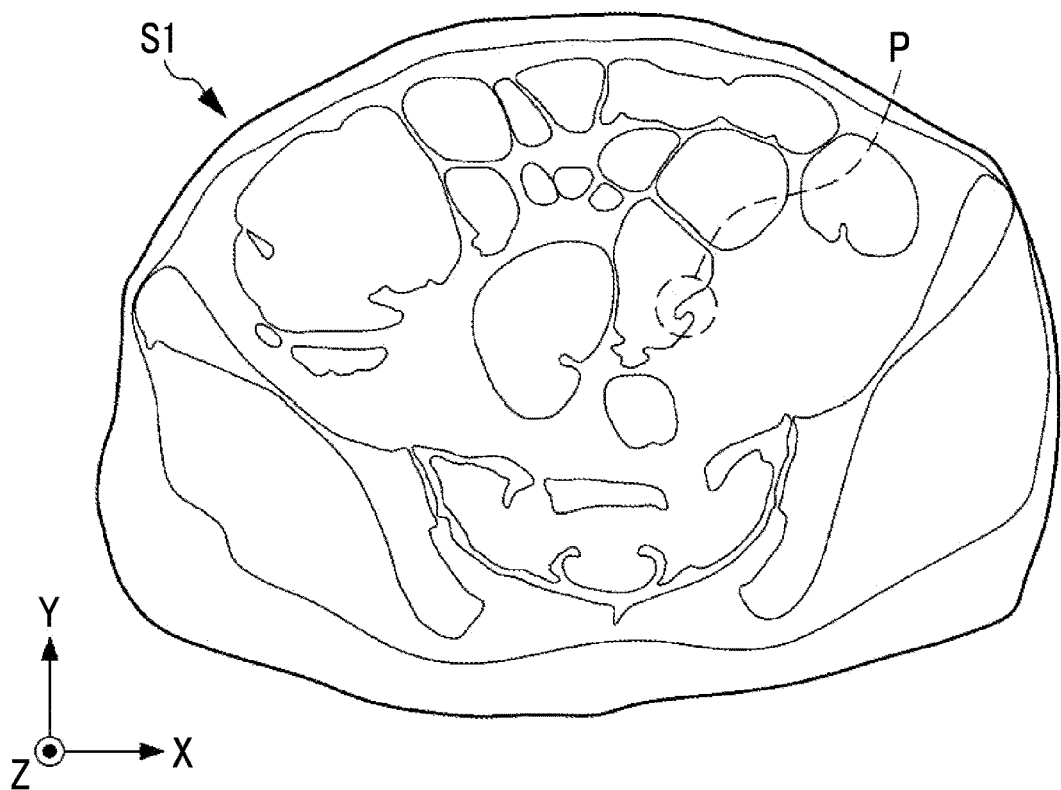
FIG. 3 is a diagram showing an example of a first input image.
Figure 4:
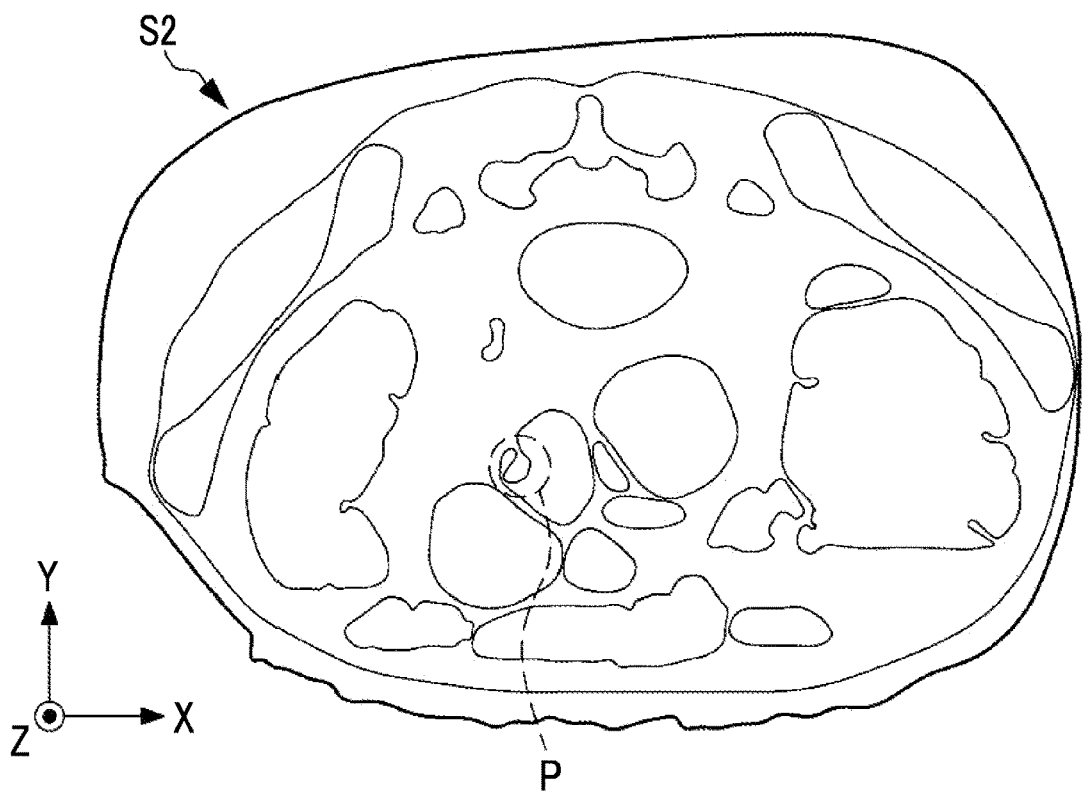
FIG. 4 is a diagram showing an example of a second input image.

In the present embodiment, for the sake of description, for example, the tomographic image showing one tomographic plane forming the three-dimensional image acquired by the CT apparatus is used as the first input image S1 and the second input image S2, but the present disclosure is not limited to this. FIGS. 3 and 4 show the first input image S1 and the second input image S2 obtained by imaging the same subject, respectively. In FIGS. 3 and 4, a Z-axis direction is a body axis direction of the subject. The first input image S1 and the second input image S2 are tomographic images showing the tomographic planes of an XY plane orthogonal to the Z-axis direction, respectively.

The first input image S1 and the second input image S2 shown in FIGS. 3 and 4 are the supine image and the prone image of a region including the large intestine, and include a polyp P of colorectal cancer as a lesion.

The object detection unit 22 detects a specific object (polyp P in the present embodiment) included in the first input image S1 and the second input image S2 based on the first input image S1 and the second input image S2. The display control unit 23 displays the first input image S1 and the second input image S2 on the display unit 14 such that a user can recognize a detection region of the specific object in each image.

Figure 5:
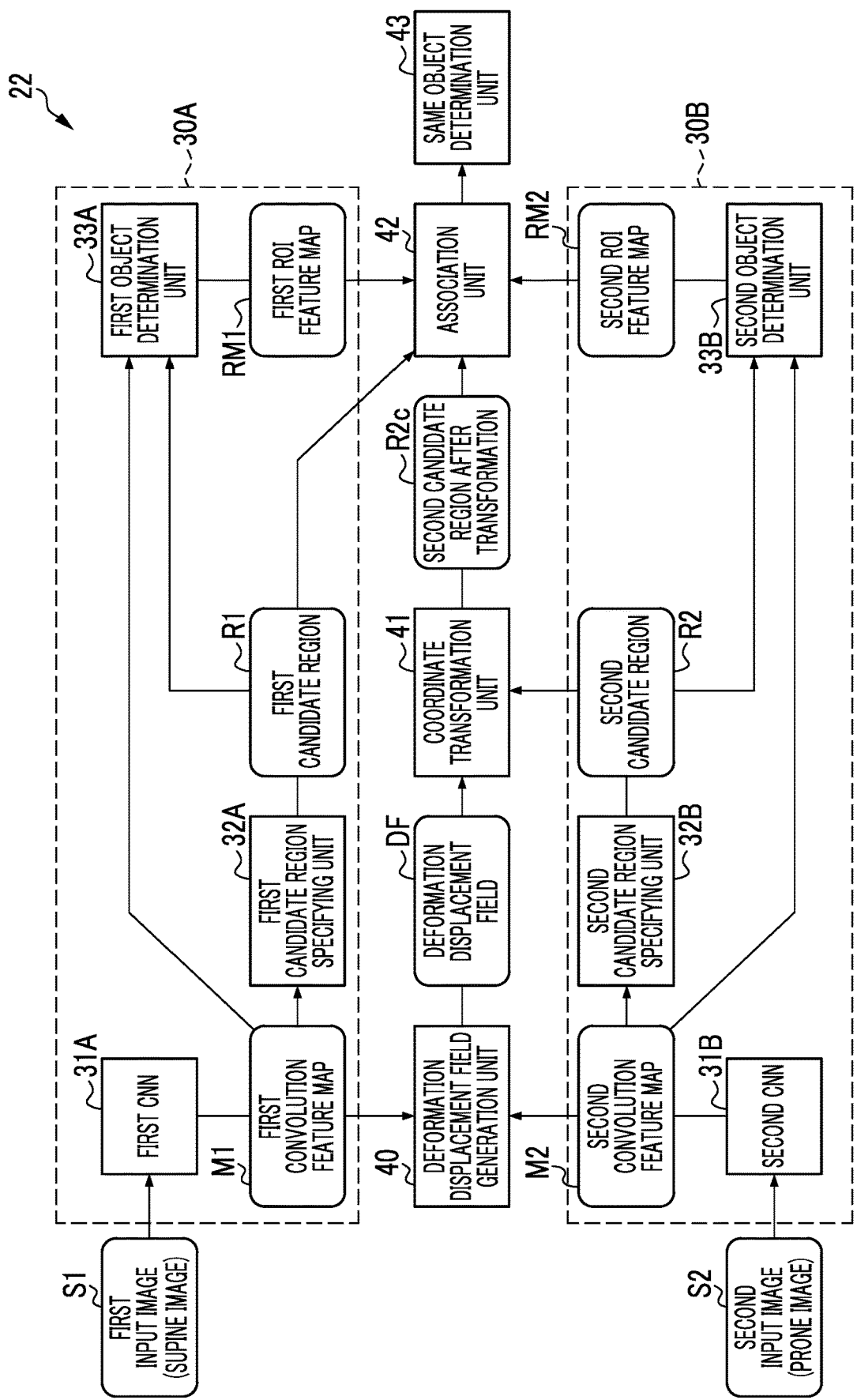
FIG. 5 is a block diagram showing a functional configuration of an object detection unit.

FIG. 5 is a block diagram showing a functional configuration of the object detection unit 22. The object detection unit 22 includes a first object identification unit 30A, a second object identification unit 30B, a deformation displacement field generation unit 40, a coordinate transformation unit 41, an association unit 42, and a same object determination unit 43.

The first object identification unit 30A performs an object identification process based on the first input image S1. The second object identification unit 30B performs the object identification process based on the first input image S1. Each of the first object identification unit 30A and the second object identification unit 30B are networks composed of Faster-RCNN. The Faster-RCNN comprises a region proposal network (RPN) that estimates a candidate region of the object from a feature map generated by the CNN. The first object identification unit 30A and the second object identification unit 30B have been trained in advance using teacher input image.

The first object identification unit 30A includes a first CNN 31A, a first candidate region specifying unit 32A, and a first object determination unit 33A. The second object identification unit 30B has the same configuration as the first object identification unit 30A, and includes a second CNN 31B, a second candidate region specifying unit 32B, and a second object determination unit 33B.

Each of the first CNN 31A and the second CNN 31B include a plurality of layers, such as a convolutional layer, a pooling layer, and a deconvolutional layer. The convolutional layer generates the feature map by performing a convolution operation that applies a filter (also called a kernel) to each pixel of the input image. The pooling layer reduces a size of the feature map by performing a process of calculating the local statistic of the feature map. An average value, a maximum value, an intermediate value, or the like is used as the statistic.

In a case in which the first input image S1 is input, the first CNN 31A outputs a convolution feature map (hereinafter, referred to as a first convolution feature map M1) to which the feature of the first input image S1 is mapped. Similarly, in a case in which the second input image S2 is input, the second CNN 31B outputs a convolution feature map (hereinafter referred to as a second convolution feature map M2) to which the feature of the second input image S2 is mapped.

Since each of the first CNN 31A and the second CNN 31B according to the present embodiment includes the convolutional layer and the pooling layer, and the pooling is performed, a size of the first convolution feature map M1 is smaller than a size of the first input image S1. For example, in a case in which the pooling layer compresses four pixels into one pixel, the size of the first convolution feature map M1 is ¼ of the size of the first input image S1. In a case in which there are two pooling layers, the size of the first convolution feature map M1 is 1/16 of the size of the first input image S1. The same applies to a relationship between the second convolution feature map M2 and the second input image S2.

It should be noted that the first CNN 31A and the second CNN 31B do not have to include the pooling layer. In this case, the sizes of the first convolution feature map M1 and the second convolution feature map M2 are the same as the sizes of the first input image S1 and the second input image S2, respectively. Here, as the CNN, a known model, such as "Zeiler and Fergus model" or "Simonyan and Zisserman model", can be used.

The first candidate region specifying unit 32A specifies a candidate region (hereinafter, referred to as a first candidate region R1) including some object from the first convolution feature map M1. Similarly, the second candidate region specifying unit 32B specifies a candidate region (hereinafter, referred to as a second candidate region R2) including some object from the second convolution feature map M2.

Each of the first candidate region specifying unit 32A and the second candidate region specifying unit 32B are composed of the RPN. The RPN has a function of estimating the candidate region of the object included in the convolution feature map. Specifically, the RPN outputs one or more candidate regions to which a score indicating the object-likeness is given for each local region of the convolution feature map. It is a feature of Faster-RCNN to comprise the RPN.

Figure 6:
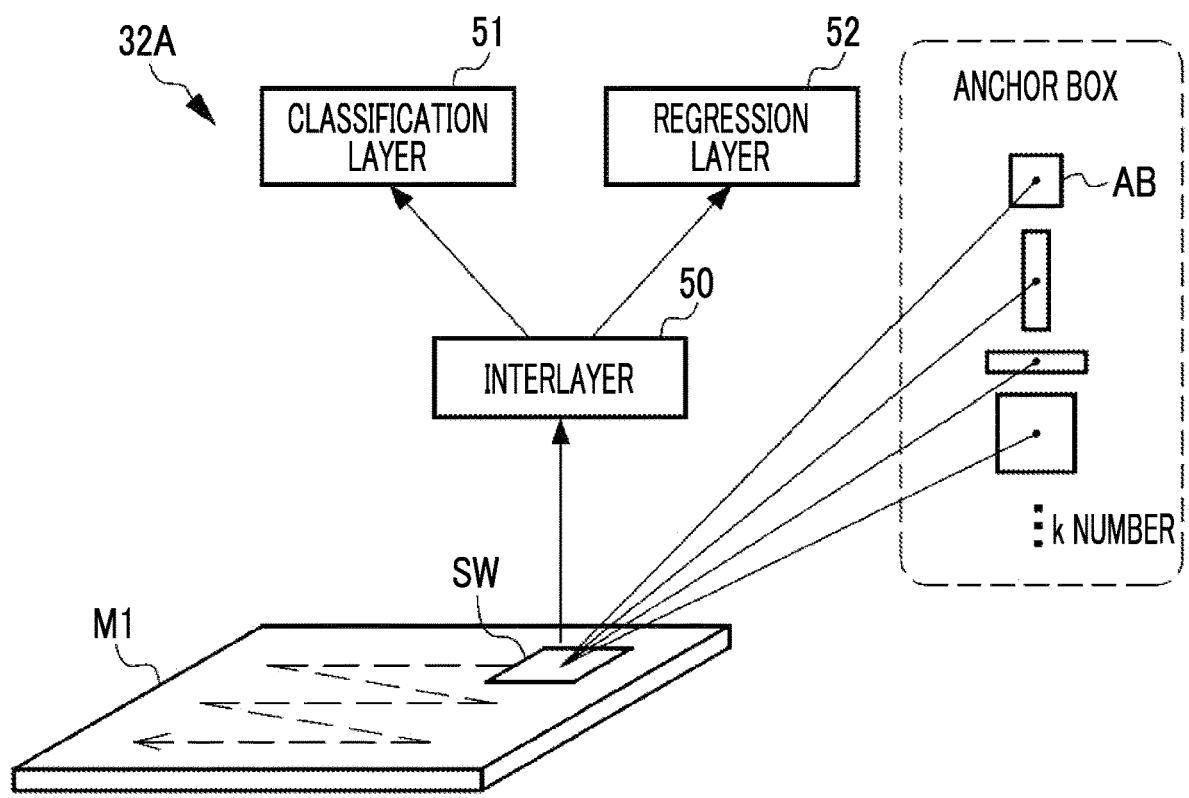
FIG. 6 is a diagram showing a configuration of a first candidate region specifying unit.

FIG. 6 is a diagram showing a configuration of the first candidate region specifying unit 32A. Since the first candidate region specifying unit 32A and the second candidate region specifying unit 32B have the same configuration, in the following, only the configuration of the first candidate region specifying unit 32A will be described.

The first candidate region specifying unit 32A is composed of a neural network including an interlayer 50, a classification layer 51, and a regression layer 52.

As shown in FIG. 6, the first candidate region specifying unit 32A selects and slides the local region of the first convolution feature map M1 by a sliding window SW. Moreover, the first candidate region specifying unit 32A creates k anchor boxes AB with the center of each sliding window SW as an anchor. The anchor box AB is a rectangular region with various aspect ratios and various sizes. For example, the anchor box AB with a total of k=9 consisting of three aspect ratios (1:1, 1:2, and 2:1) and three sizes (128×128, 256×256, and 512×512) is created. These k anchor boxes AB are input to the classification layer 51 and the regression layer 52 via the interlayer 50.

The interlayer 50 calculates a feature vector in each anchor box AB. The feature vector is composed of, for example, an average value, a maximum value, an intermediate value, or the like.

The classification layer 51 and the regression layer 52 make predictions based on the feature amount calculated by the interlayer 50. The classification layer 51 outputs a score indicating the presence or absence of the object for each anchor box AB. The regression layer 52 outputs an offset value (shift amount) of a position (X coordinate and Y coordinate of the center) and a size (height and width) for each anchor box AB. It is assumed that k anchor boxes AB are set for one sliding window SW, the classification layer 51 outputs a 2k-dimensional vector, and the regression layer 52 outputs a 4k-dimensional vector.

The first candidate region specifying unit 32A learns by minimizing a multitasking loss, which is the sum of a loss relating to the classification of the presence or absence of the object and a loss relating to the position and the size of a bounding box, based on the teacher input image. The trained first candidate region specifying unit 32A specifies the anchor box AB with the highest certainty for each object candidate as the first candidate region R1 based on the first convolution feature map M1. Specifically, in order to generate the first candidate region R1, unnecessary anchor box AB is deleted by suppressing a non-maximum value from the scored anchor box AB.

Returning to FIG. 5, the first object determination unit 33A determines whether or not the object candidate included in each first candidate region R1 is the specific object (polyp P) based on the first convolution feature map M1 and the first candidate region R1 specified by the first candidate region specifying unit 32A. Similarly, the second object determination unit 33B determines whether or not the object candidate included in each second candidate region R2 is the specific object (polyp P) based on the second convolution feature map M2 and the second candidate region R2 specified by the second candidate region specifying unit 32B.

Figure 7:
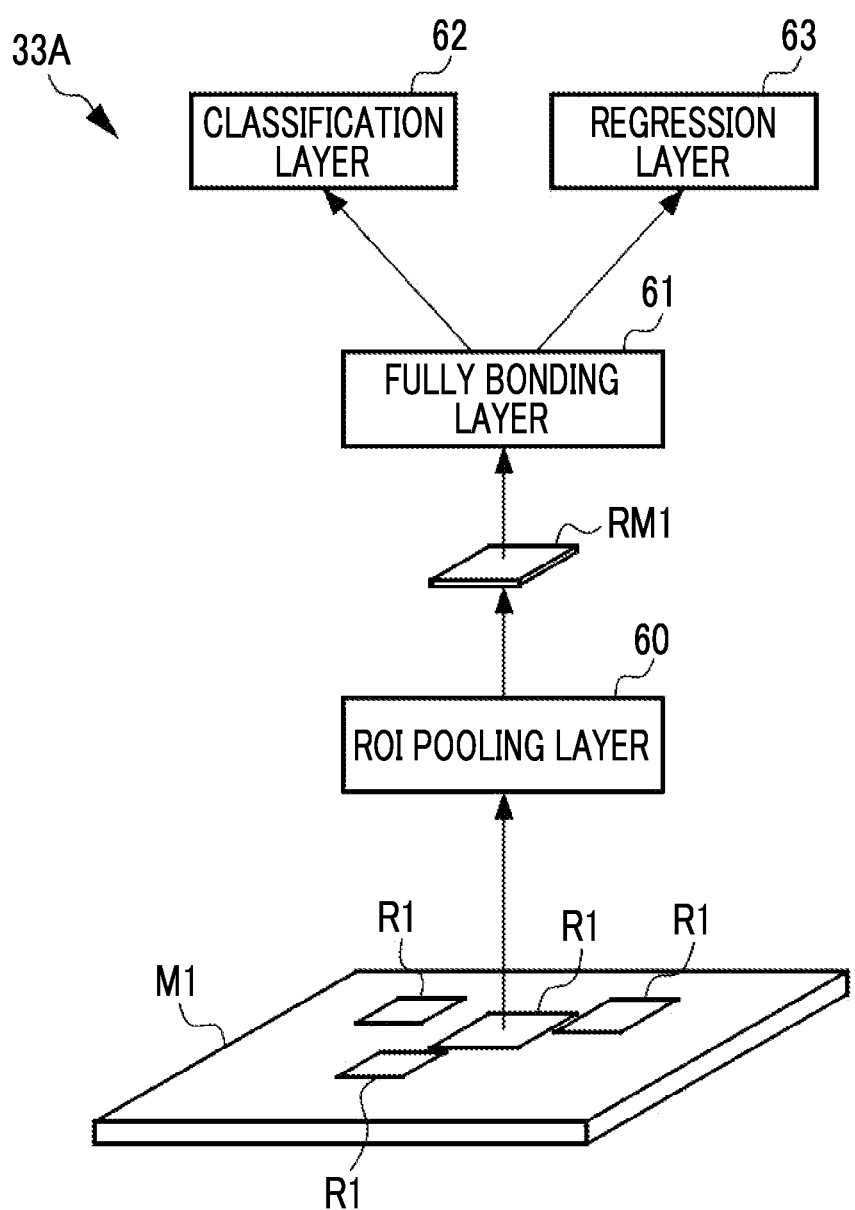
FIG. 7 is a diagram showing a configuration of a first object determination unit.

FIG. 7 is a diagram showing a configuration of the first object determination unit 33A. Since the first object determination unit 33A and the second object determination unit 33B have the same configuration, in the following, only the configuration of the first object determination unit 33A will be described.

As shown in FIG. 7, the first object determination unit 33A is composed of a neural network including a region of interest (ROI) pooling layer 60, a fully bonding layer 61, a classification layer 62, and a regression layer 63. The first object determination unit 33A outputs a score indicating the certainty that the object candidate is the specific object for each of a plurality of first candidate regions R1 specified by the first candidate region specifying unit 32A.

The plurality of first candidate regions R1 specified by the first candidate region specifying unit 32A have different aspect ratios and various numbers of dimensions. Therefore, the ROI pooling layer 60 performs a process of transforming the feature map having a different number of dimensions into a vector having a fixed size for each first candidate region R1. Specifically, the feature map in each first candidate region R1 is cut out from the first convolution feature map M1, and then input to the ROI pooling layer 60. The ROI pooling layer 60 transforms the input feature map and outputs the transformed feature map as a first ROI feature map RM1.

The fully bonding layer 61 calculates a feature amount of the first ROI feature map RM1. The classification layer 62 and the regression layer 63 make predictions based on the feature calculated by the fully bonding layer 61. The classification layer 62 outputs a score (hereinafter referred to as a first sub-score SC1) indicating the certainty that the object candidate is the specific object by class recognition for each first ROI feature map RM1. The first sub-score SC1 is represented by a numerical value that is equal to or greater than 0 and equal to or smaller than 1. As the first sub-score SC1 is closer to 1, the certainty that the object candidate included in the first candidate region R1 is the specific object is higher. The regression layer 63 outputs an offset value (shift amount) of a position (X coordinate and Y coordinate of the center) and a size (height and width) for each first candidate region R1.

The first object determination unit 33A learns using the first candidate region R1 specified by the trained first candidate region specifying unit 32A by minimizing a multitasking loss, which is the sum of a loss relating to the first sub-score SC1 and a loss relating to the position and the size of the first candidate region R1, based on the teacher input image. The trained first candidate region specifying unit 32A specifies the first candidate region R1 having the highest certainty that the object candidate is the specific object for each object candidate. In this way, the first object determination unit 33A outputs the first candidate region R1 to which the position and the size are corrected by regression and the first sub-score SC1 is attached.

Similarly, the second object determination unit 33B generates a second ROI feature map RM2 for each second candidate region R2. The second object determination unit 33B outputs a score (hereinafter referred to as a second sub-score SC2) indicating the certainty that the object candidate is the specific object for each second ROI feature map RM2, and outputs an offset value (shift amount) of a position (X coordinate and Y coordinate of the center) and a size (height and width) for each second candidate region R2. In this way, the second object determination unit 33B outputs the second candidate region R2 to which the position and the size are corrected by regression and the second sub-score SC2 is attached.

Returning to FIG. 5, the first convolution feature map M1 generated by the first CNN 31A and the second convolution feature map M2 generated by the second CNN 31B are input to the deformation displacement field generation unit 40.

Figure 8:
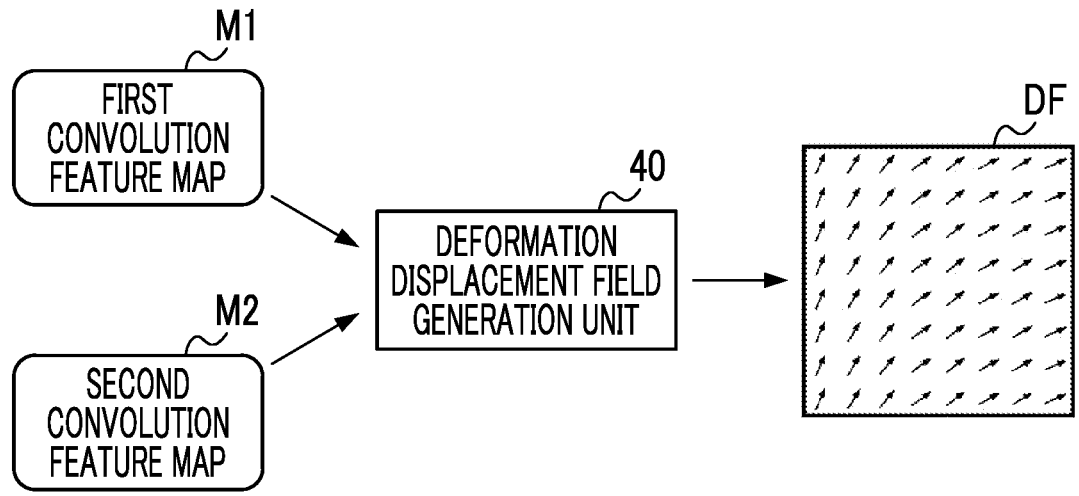
FIG. 8 is a diagram schematically showing a deformation displacement field generated by a deformation displacement field generation unit.

The deformation displacement field generation unit 40 is composed of the CNN, and learns a process of deformation registration (that is, non-rigid registration) from the second input image S2 (prone image) to the first input image S1 (supine image) by receiving the first convolution feature map M1 and the second convolution feature map M2 as inputs. For example, the final output of registration is the feature map of the same or scaled size as the first input image S1, and corresponds to a movement amount to each point of the first input image S1 corresponding to each point of the second input image S2. As shown in FIG. 8, the trained deformation displacement field generation unit 40 generates a deformation displacement field DF indicating the movement amount to each point of the first input image S1 corresponding to each point of the second input image S2 by receiving the first convolution feature map M1 and the second convolution feature map M2 as inputs.

The deformation displacement field generation unit 40 learns to generate the optimum deformation displacement field DF based on an error of the anatomically corresponding feature point between the first convolution feature map M1 and the second convolution feature map M2. Specifically, the deformation displacement field generation unit 40 learns by minimizing the loss using the error in the position of the corresponding feature point between the first convolution feature map M1 and the second convolution feature map M2 as the loss. It should be noted that the deformation displacement field generation unit 40 may learn using the error in the position of the corresponding region (for example, the region including the polyp P) between the first convolution feature map M1 and the second convolution feature map M2 and the error in the shape of the region as the loss. In the present embodiment, since the polyp in the large intestine is the detection target, the deformation displacement field generation unit 40 can generate the highly accurate deformation displacement field DF by learning the registration of the large intestine region.

Figure 9:
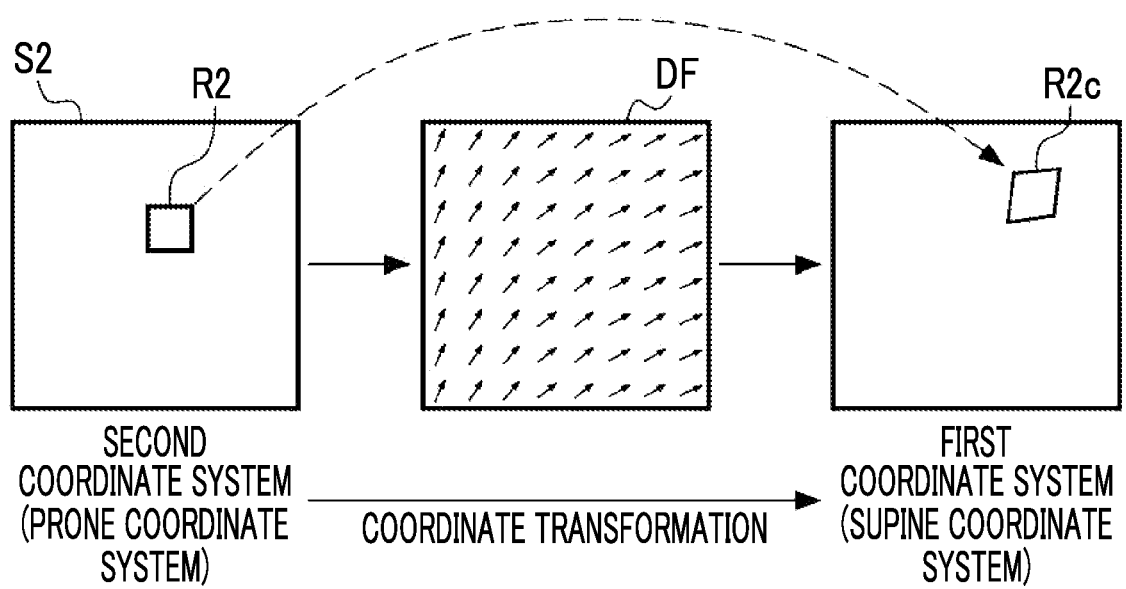
FIG. 9 is a diagram schematically showing a coordinate transformation process performed by a coordinate transformation unit.

The coordinate transformation unit 41 performs coordinate transformation of the second candidate region R2 specified by the second candidate region specifying unit 32B based on the deformation displacement field DF generated by the deformation displacement field generation unit 40. FIG. 9 is a diagram schematically showing a coordinate transformation process performed by the coordinate transformation unit 41. The coordinate transformation unit 41 performs coordinate transformation on a second coordinate system (prone coordinate system) indicating the second input image S2 into a first coordinate system (supine coordinate system) indicating the first input image S1 based on the deformation displacement field DF. As a result, the coordinate of the second candidate region R2 is transformed into the first coordinate system. The coordinate transformation unit 41 generates a second candidate region R2c after the coordinate transformation.

Figure 10:
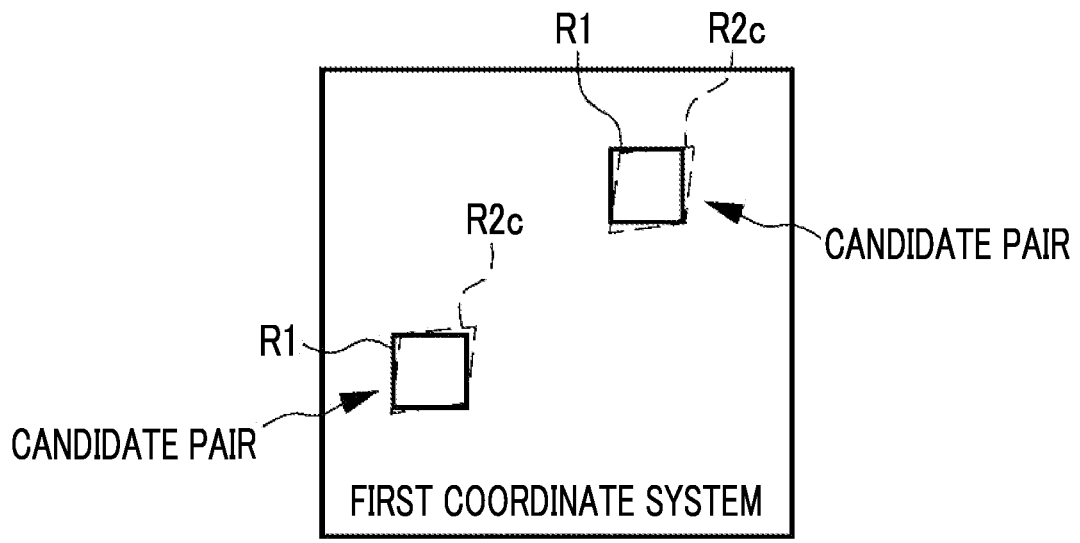
FIG. 10 is a diagram schematically showing a candidate pair associated with each other by an association unit.

The association unit 42 associates the first candidate region R1 and the second candidate region R2c, which are close to each other with each other, as a candidate pair by comparing the position of the first candidate region R1 with the position of the second candidate region R2c after the coordinate transformation by the coordinate transformation unit 41 in the first coordinate system. FIG. 10 is a diagram schematically showing the candidate pair associated with each other by the association unit 42. The association unit 42 associates, for example, the candidate pair in which a distance between the center position of the first candidate region R1 and the center position of the second candidate region R2c after the coordinate transformation is equal to or smaller than a certain value. It should be noted that the association unit 42 may associate the candidate pair in which an overlap ratio between the first candidate region R1 and the second candidate region R2c after the coordinate transformation is equal to or greater than a certain value.

In addition, the association unit 42 acquires the first ROI feature map RM1 and the second ROI feature map RM2 corresponding to the first candidate region R1 and the second candidate region R2c after the coordinate transformation, which are associated with each other, from the first object determination unit 33A and the second object determination unit 33B and associates the first ROI feature map RM1 and the second ROI feature map RM2 with each other.

The same object determination unit 43 determines whether or not the object candidates included in the first candidate region R1 and the second candidate region R2c after the coordinate transformation are the same object and are the specific object based on the first ROI feature map RM1 and the second ROI feature map RM2, which are associated with each other.

Figure 11:
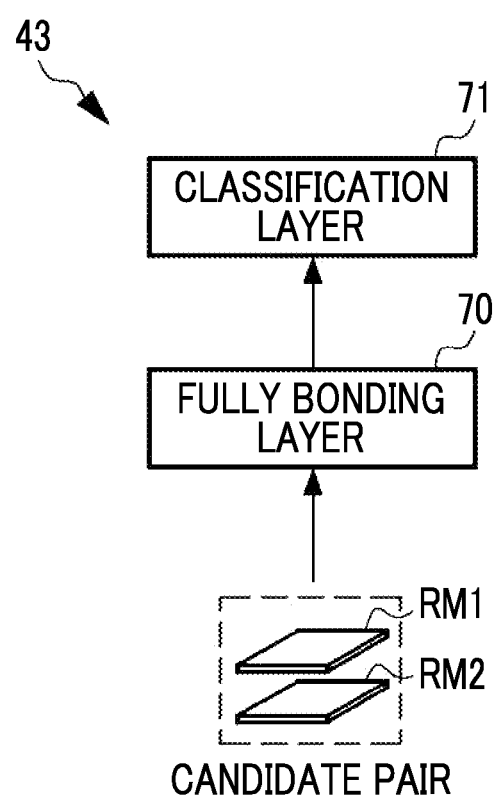
FIG. 11 is a diagram showing a configuration of a same object determination unit.

FIG. 11 is a diagram showing a configuration of the same object determination unit 43. The same object determination unit 43 is composed of a neural network including a fully bonding layer 70 and a classification layer 71. The fully bonding layer 70 calculates the feature amounts of the first ROI feature map RM1 and the second ROI feature map RM2, which are associated with each other as the candidate pair.

The classification layer 71 outputs a score (hereinafter, referred to as a main score SC0) indicating the certainty that the object candidates included in the first candidate region R1 and the second candidate region R2c after the coordinate transformation are the same object and are the specific object by performing class recognition based on the feature amounts calculated by the fully bonding layer 70. The main score SC0 is represented by a numerical value that is equal to or greater than 0 and equal to or smaller than 1. As the main score SC0 is closer to 1, the certainty that the object candidates included in the first candidate region R1 and the second candidate region R2c after the coordinate transformation are the same object and are the specific object is higher.

Figure 12:
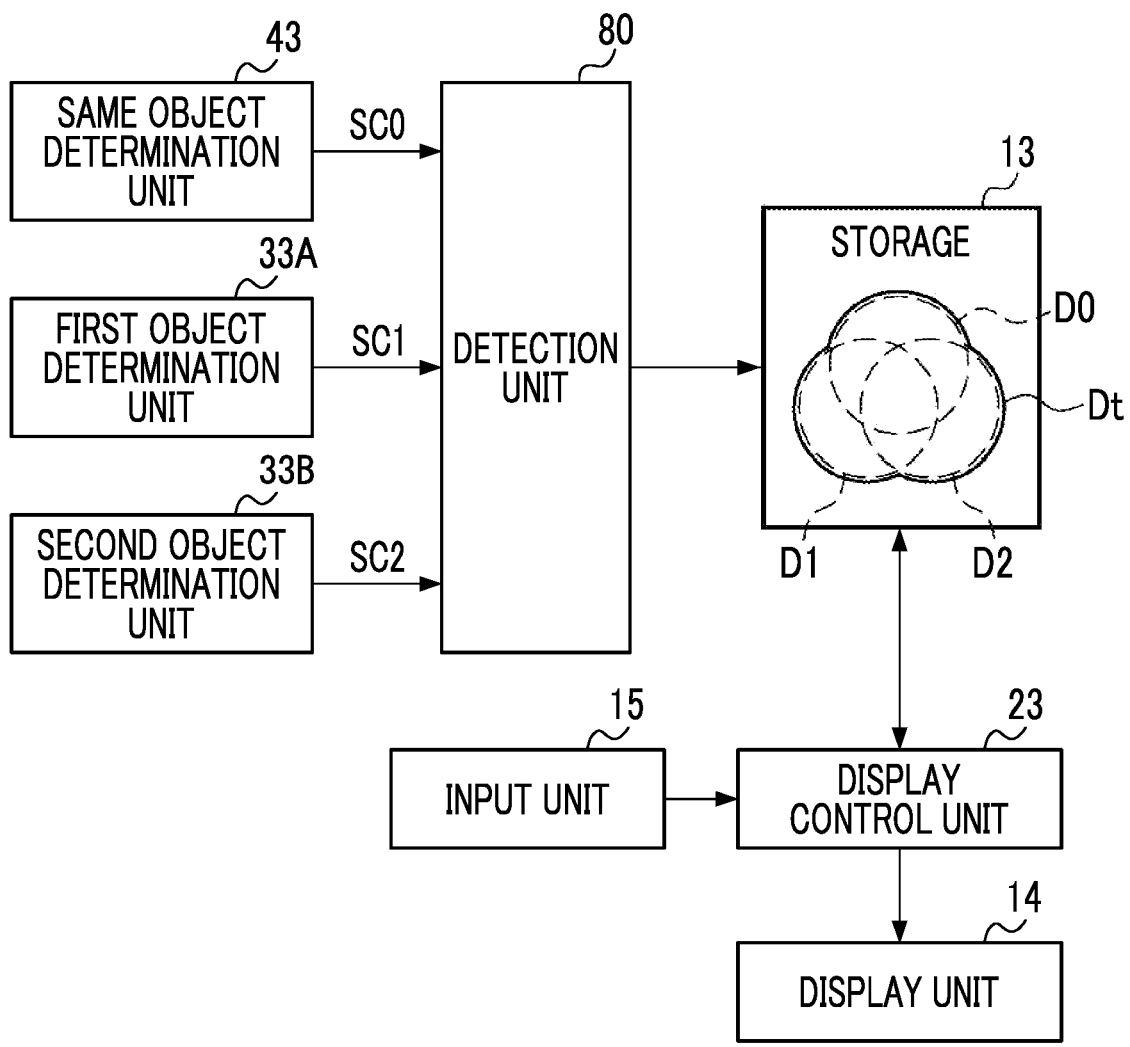
FIG. 12 is a diagram showing a configuration of a detection unit.

As shown in FIG. 12, the object detection unit 22 includes a detection unit 80 that detects the specific object based on the score output from each of the same object determination unit 43, the first object determination unit 33A, and the second object determination unit 33B. The detection unit 80 records region information of the object candidate detected as the specific object in the storage 13 as detection data. The display control unit 23 causes the display unit 14 to display the detection data, the image, and the like stored in the storage 13 based on an input operation signal from the input unit 15.

Figure 13:
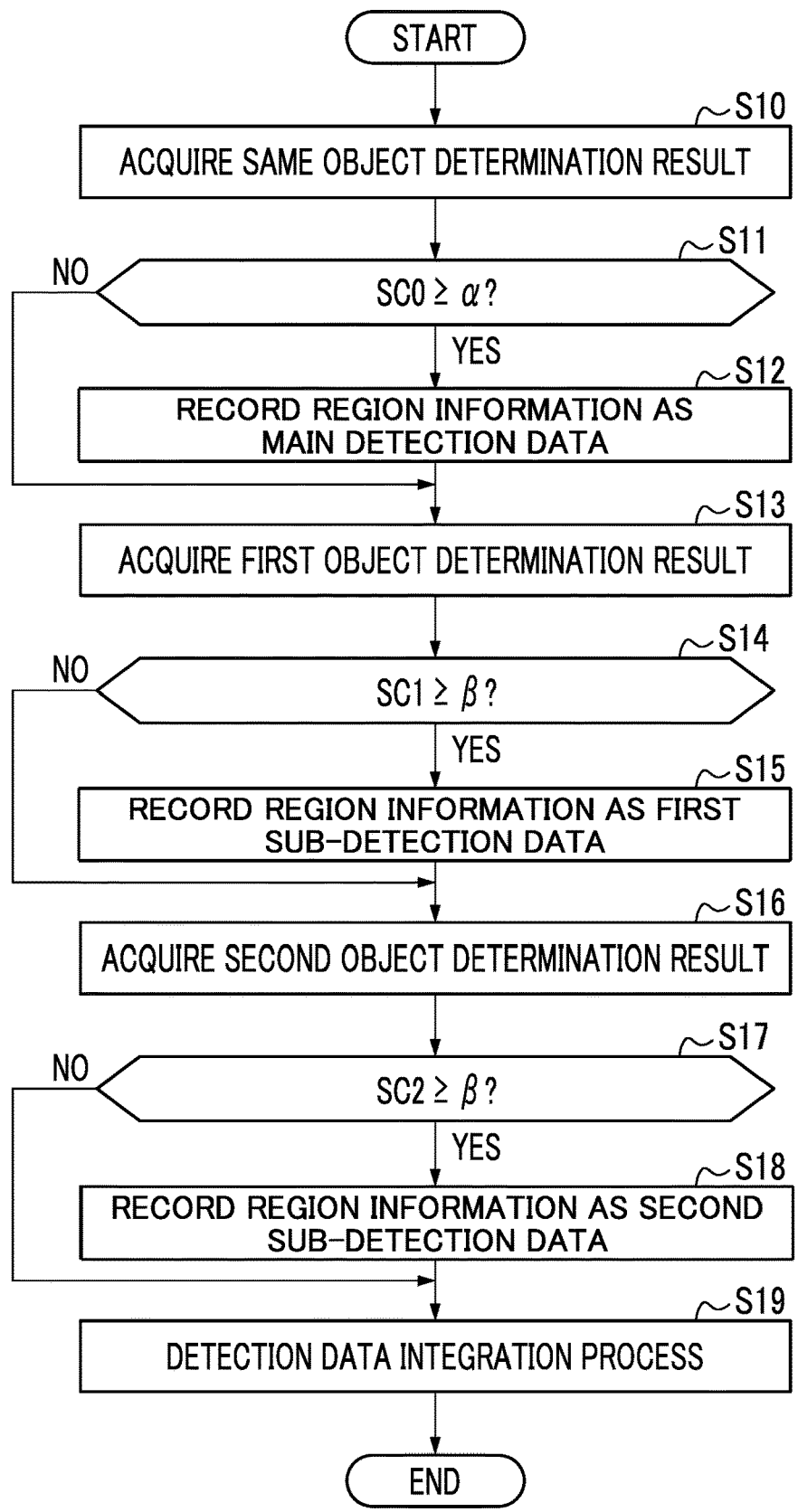
FIG. 13 is a flowchart showing a detection process by the detection unit.

Then, a detection process of a lesion region by the detection unit 80 will be described with reference to a flowchart shown in FIG. 13. In the following detection process, the detection is performed based on the first sub-score SC1 and the second sub-score SC2 in addition to the main score SC0, so that the detection omission is reduced while maintaining high detection accuracy.

First, the detection unit 80 acquires a determination result (same object determination result) including the main score SC0 from the same object determination unit 43 (step S10). The detection unit 80 compares the acquired main score SC0 with a first threshold value $\alpha$ (step S11). In a case in which the main score SC0 is equal to or greater than the first threshold value $\alpha$ (step S11: YES), the detection unit 80 records the region information of the object candidate having the main score SC0 in the storage 13 as main detection data D0 (step S12). On the other hand, in a case in which the main score SC0 is smaller than the first threshold value $\alpha$ (step S11: NO), the detection unit 80 advances the process to step S13 without performing a recording process. It should be noted that, in a case in which there are a plurality of candidate pairs, the detection unit 80 repeats the processes of steps S10 to S12.

Then, the detection unit 80 acquires a determination result (first object determination result) including the first sub-score SC1 from the first object determination unit 33A (step S13). The detection unit 80 compares the acquired first sub-score SC1 with a second threshold value $\beta$ (step S14). Here, the second threshold value $\beta$ is a value greater than the first threshold value $\alpha$ (that is, $\beta > \alpha$). Since the first sub-score SC1 output from the first object determination unit 33A is considered to be less accurate than the main score SC0 output from the same object determination unit 43, the detection is performed by using the second threshold value $\beta$ having the detection conditions stricter than the first threshold value $\alpha$.

In a case in which the first sub-score SC1 is equal to or greater than the second threshold value $\beta$ (step S14: YES), the detection unit 80 records the region information of the object candidate having the first sub-score SC1 in the storage 13 as first sub-detection data D1 (step S15). On the other hand, in a case in which the first sub-score SC1 is smaller than the second threshold value $\beta$ (step S14: NO), the detection unit 80 advances the process to step S16 without performing the recording process. It should be noted that, in a case in which there are a plurality of first candidate regions R1, the detection unit 80 repeats the processes of steps S13 to S15.

Then, the detection unit 80 acquires a determination result (second object determination result) including the second sub-score SC2 from the second object determination unit 33B (step S16). The detection unit 80 compares the acquired second sub-score SC2 with the second threshold value $\beta$ (step S17). In a case in which the second sub-score SC2 is equal to or greater than the second threshold value $\beta$ (step S17: YES), the detection unit 80 records the region information of the object candidate having the second sub-score SC2 in the storage 13 as second sub-detection data D2 (step S18). On the other hand, in a case in which the second sub-score SC2 is smaller than the second threshold value $\beta$ (step S17: NO), the detection unit 80 advances the process to step S19 without performing the recording process. It should be noted that, in a case in which there are a plurality of second candidate regions R2, the detection unit 80 repeats the processes of steps S16 to S18.

Moreover, in step S19, the detection unit 80 generates integrated detection data Dt obtained by eliminating overlap of the main detection data D0, the first sub-detection data D1, and the second sub-detection data D2 recorded in the storage 13, and integrating the data as union data.

It should be noted that the order of the three determination processes of the main score SC0, the first sub-score SC1, and the second sub-score SC2 by the detection unit 80 is not limited to the order described above, and can be optionally changed. In addition, it is also possible to perform these three determination processes in parallel.

Figure 14:
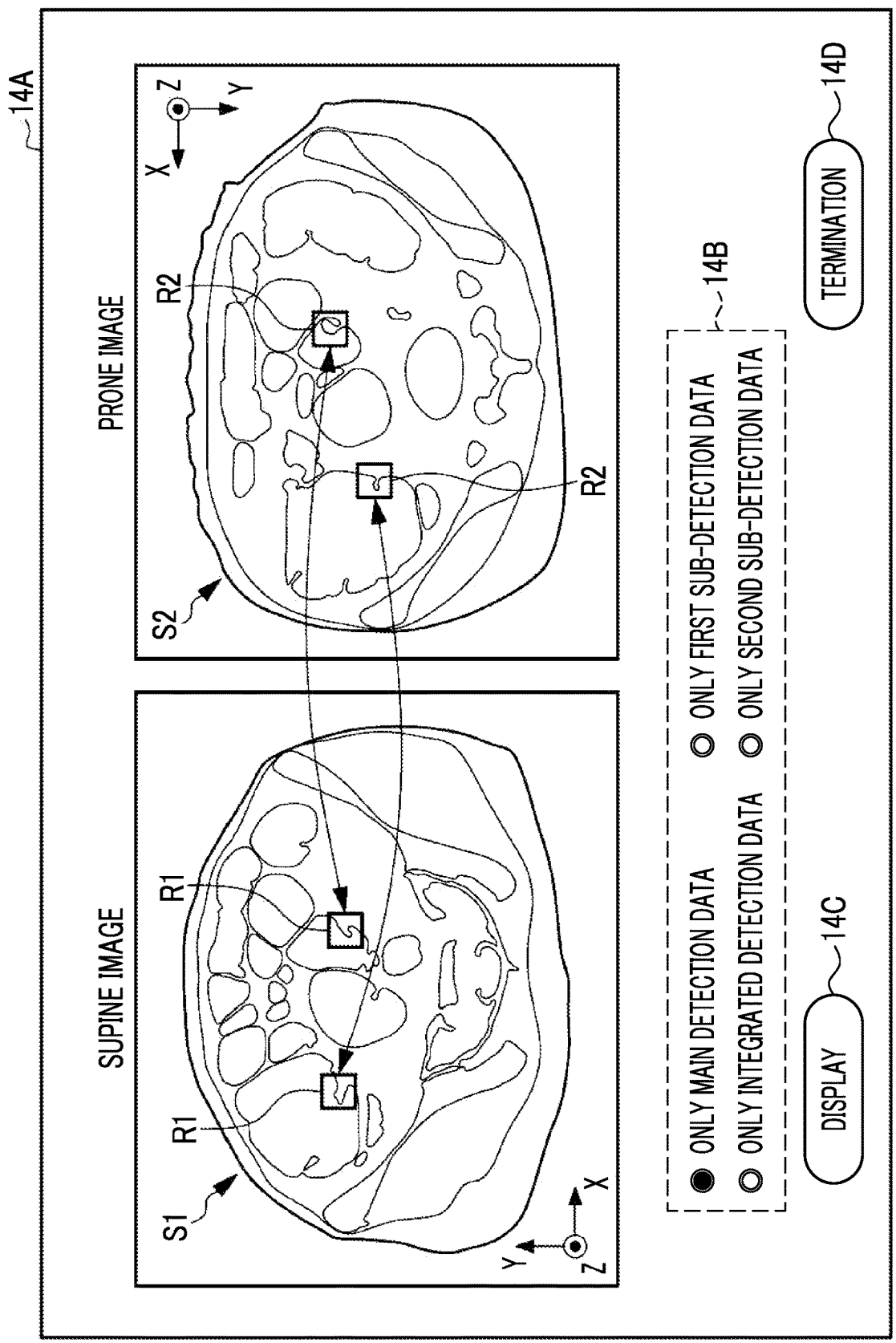
FIG. 14 is a diagram showing a display screen of a display unit.

FIG. 14 is a diagram showing a display screen 14A of the display unit 14. As shown in FIG. 14, on the display screen 14A, the first input image S1 as the supine image and the second input image S2 as the prone image are displayed in a state of being adjacent to each other in a comparable manner. It should be noted that, in FIG. 14, the coordinate system of the second input image S2 is rotated by 180 degrees.

On the display screen 14A, the candidate region (lesion region) having high certainty to include the specific object is displayed based on any of the four types of detection data (main detection data D0, first sub-detection data D1, second sub-detection data D2, and integrated detection data Dt) recorded in the storage 13.

In addition, the display control unit 23 displays a user interface on the display screen 14A such that the user can select which of the four types of detection data to display the candidate region. On the display screen 14A, for example, a selection button 14B for selecting four types of detection data by a mouse as the input unit 15, a display button 14C for executing display, and a termination button 14D for terminating the display are displayed. The user can display the candidate region corresponding to desired detection data by performing a selection operation of the selection button 14B and clicking the display button 14C.

FIG. 14 is a display example in a case in which the main detection data D0 is selected. In this case, on the display screen 14A, the first candidate region R1 and the second candidate region R2 including the same specific object detected based on the main score SC0 are displayed in a state of being associated with each other.

In addition, in a case in which the integrated detection data Dt is selected, all the candidate regions detected by the detection unit 80 are displayed. In addition, in a case in which the first sub-detection data D1 is selected, the first candidate region R1 detected based on the first sub-score SC1 is displayed. In a case in which the second subdetection data D2 is selected, the second candidate region R2 detected based on the second sub-score SC2 is displayed.

According to the embodiment described above, since it is determined that the object candidates included in the first candidate region R1 and the second candidate region R2c after the coordinate transformation, which are associated with each other as the candidate pair, are the same object and are specific object, it is possible to reduce the false detection of the specific object (polyp) than the related art.

For example, in the related art, in a case in which water droplets are attached to the lumen of the large intestine, there is a risk that water droplets appears in the image as a convex part of the lumen of the large intestine and is falsely detected as the polyp. Since water droplets are detached or deformed by changing the posture of the subject, such water droplets do not appear in the corresponding regions in the two input images. In the embodiment described above, since the determination is made based on the two candidate regions associated with each other in the two input images obtained by imaging the subject in different postures, a risk of the false detection of water droplets or the like as the specific object is reduced, and the specific object can be detected with high accuracy.

In addition, in the lumen of the large intestine, the polyp may be hidden by residues, such as stool. In this case, by changing the posture of the subject, the residue may be detached and the polyp may appear. In such a case, in a case in which the determination is made based on the two candidate regions as described above, since the same object is not present in the two candidate regions, there is a possibility that the polyp is not detected. On the other hand, in the embodiment described above, since the determination based on the candidate region in each input image obtained in each posture is also performed, it is possible to suppress the detection omission of the polyp due to the residue. In this way, according to the embodiment described above, the detection omission can be reduced while maintaining high detection accuracy.

In addition, in the embodiment described above, since the object detection unit 22 performs the detection of the specific object and the deformation registration between the two input images in a partially common network, learning can be performed with one algorithm and the detection time can be shortened. Further, the object detection unit 22 can learn using only the correct answer data relating to the position of the specific object and the pair of the specific objects in the two input images.

Modification Example

Hereinafter, a modification example of the embodiment described above will be described. In the embodiment described above, the first object identification unit 30A and the second object identification unit 30B in the object detection unit 22 are composed of the Faster-RCNN, but are not limited to the Faster-RCNN, and may be composed of the Fast-RCNN or the RCNN. In addition, the object detection unit 22 is not limited to the neural network, and may be composed of, for example, a support vector machine or a supervised learning algorithm, such as a decision tree.

In addition, in the embodiment described above, the object detection unit 22 comprises the first CNN 31A and the second CNN 31B, but does not have to comprise the first CNN 31A and the second CNN 31B. In this case, the first candidate region specifying unit 32A and the second candidate region specifying unit 32B need only specify the first candidate region R1 and the second candidate region R2 from the first input image S1 and the second input image S2, respectively. In addition, in this case, the first object determination unit 33A and the second object determination unit 33B need only cut out the first candidate region R1 and the second candidate region R2 from the first input image S1 and the second input image S2, respectively, to determine the category of the object. Further, in this case, the deformation displacement field generation unit 40 need only generate the deformation displacement field DF by receiving the first input image S1 and the second input image S2 as inputs.

In addition, in the embodiment described above, the same object determination unit 43 determines the category of the object based on the first ROI feature map RM1 and the second ROI feature map RM2. Instead of this, the same object determination unit 43 may determine the category of the object based on the first candidate region R1 cut out from the first input image S1 and the second candidate region R2c cut out from the second input image S2 and coordinate-transformed by the coordinate transformation unit 41.

In addition, in the embodiment described above, the main score SC0 is set to a value equal to or greater than 0 and equal to or smaller than 1, and each of the first sub-score SC1 and the second sub-score SC2 is set to a value equal to or greater than 0 and equal to or smaller than 1, but an upper limit and a lower limit of each score do not have to the same. In this case, the second threshold value β need only have the detection condition stricter than the first threshold value α. That is, the fact that the second threshold value β is greater than the first threshold value α means that the second threshold value β is greater than the first threshold value α in a case in which the upper limit and lower limit of each score are set to the same and represented by the same scale.

In addition, in the embodiment described above, the object detection is performed based on the two input images obtained by imaging the subject in two different postures, but the object detection can be performed based on three or more input images obtained by imaging the same subject in three or more different postures.

Figure 15:
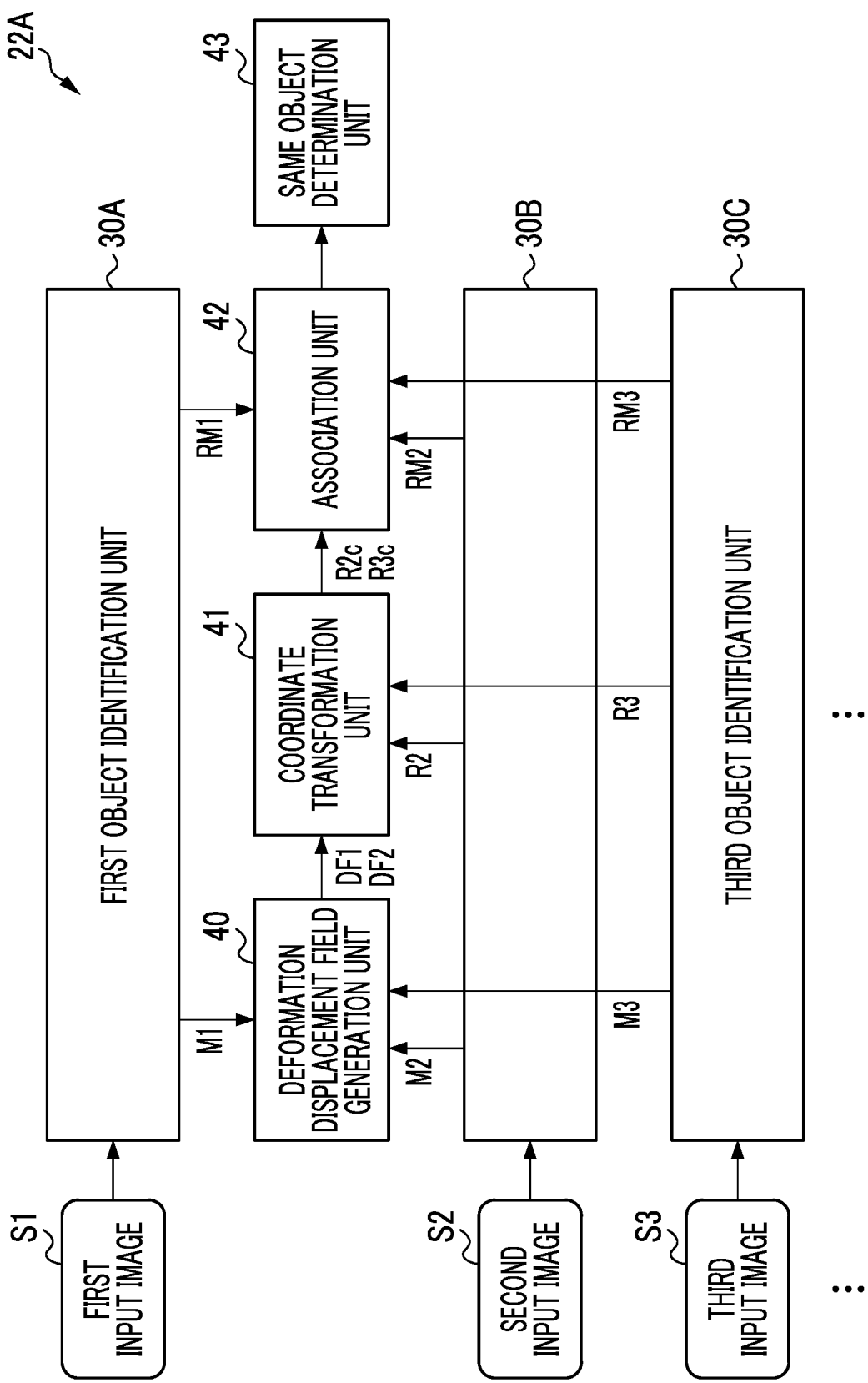
FIG. 15 is a diagram showing a configuration of an object detection unit according to a modification example.

FIG. 15 is a diagram showing a configuration of an object detection unit 22A according to the modification example. The object detection unit 22A performs the object detection based on three or more input images obtained by imaging the same subject in three or more different postures. The object detection unit 22A comprises as many object identification units as the number corresponding to the number of input images.

For example, in a case in which the first input image S1, the second input image S2, and a third input image S3 are input, the object detection unit 22A comprises a third object identification unit 30C in addition to the first object identification unit 30A and the second object identification unit 30B according to the embodiment described above. The third object identification unit 30C has the same configuration as the second object identification unit 30B. The third object identification unit 30C generates a third convolution feature map M3, a third candidate region R3, a second object, and a third ROI feature map RM3 in a process of the object identification based on the third input image S3.

In the present modification example, the deformation displacement field generation unit 40 generates a second deformation displacement field DF2 indicating the movement amount to each point of the first input image S1 corresponding to each point of the third input image S3 in addition to a first deformation displacement field DF1 indicating the movement amount to each point of the first input image S1 corresponding to each point of the second input image S2. In addition, in the present modification example, the coordinate transformation unit 41 performs the coordinate transformation of the third candidate region R3 based on the second deformation displacement field DF2 in addition to performing the coordinate transformation of the second candidate region R2 based on the first deformation displacement field DF1. That is, the coordinate transformation unit 41 generates a third candidate region R3c after the coordinate transformation in addition to the second candidate region R2c after the coordinate transformation.

In addition, in the present modification example, the association unit 42 compares the position of the first candidate region R1, the position of the second candidate region R2c after the coordinate transformation, and the position of the third candidate region R3c after the coordinate transformation in the first coordinate system. Moreover, the association unit 42 associates the first candidate region R1, the second candidate region R2c, and the third candidate region R3c, which are close to each other, as a candidate group. In addition, the association unit 42 associates the first ROI feature map RM1, the second ROI feature map RM2, and the third ROI feature map RM3 corresponding to the first candidate region R1, the second candidate region R2c, and the third candidate region R3c, which are associated with each other.

Moreover, the same object determination unit 43 determines whether or not the object candidates included in the candidate regions are the same object and are the specific object based on the first ROI feature map RM1, the second ROI feature map RM2, and the third ROI feature map RM3 which are associated with each other.

In addition, in the present modification example, the third object identification unit 30C outputs a score (hereinafter, referred to as a third sub-score SC3) indicating the certainty that the object candidate is the specific object. The detection unit 80 performs the detection based on the third sub-score SC3 in addition to the main score SC0, the first sub-score SC1, and the second sub-score SC2 described above, and generates third sub-detection data D3.

In a case in which the object detection is performed based on four or more input images, the configuration of the object detection unit can be similarly changed.

It should be noted that the configurations of the modification examples can be appropriately combined as long as no contradiction occurs.

In addition, in the embodiment described above and the modification example, for example, as a hardware structure of a processing unit, which executes various processes, such as the image acquisition unit 21, the object detection units 22 and 22A, the display control unit 23, the following various processors can be used. The various processors described above include, for example, a programmable logic device (PLD) that is a processor of which a circuit configuration can be changed after manufacture, such as a field-programmable gate array (FPGA), and a dedicated electric circuit that is a processor having a dedicated circuit configuration designed to execute a specific process, such as an application specific integrated circuit (ASIC), in addition to the CPU that is a general-purpose processor which executes software (operation program) to function as various processing units as described above.

One processing unit may be configured by one of these various processors, or may be configured by a combination of two or more processors having the same type or different types (for example, a combination of a plurality of FPGAs or a combination of a CPU and an FPGA). In addition, a plurality of processing units may be configured by one processor.

As an example of the configuration in which a plurality of processing units are configured by one processor, first, as represented by the computer, such as a client and a server, there is an aspect in which one processor is configured by a combination of one or more CPUs and software, and this processor functions as a plurality of processing units. Secondly, as represented by a system on chip and the like, there is an aspect in which a processor that realizes the functions of the entire system including a plurality of processing units by one integrated circuit (IC) chip is used. In this way, various processing units are configured by using one or more of the various processors as the hardware structure.

Further, as the hardware structure of the various processors, more specifically, an electric circuit (circuitry) in which circuit elements, such as semiconductor elements, are combined can be used.

From the above description, the invention described in the following supplementary notes 1 to 5 can be grasped.

Supplementary Note 1

An object detection device that detects a specific object included in an input image, the device comprising a first candidate region specifying processor that specifies a first candidate region in which an object candidate is included from a first input image obtained by imaging a subject in a first posture, a second candidate region specifying processor that specifies a second candidate region in which an object candidate is included from a second input image obtained by imaging the subject in a second posture different from the first posture, a deformation displacement field generation processor that generates a deformation displacement field between the first input image and the second input image, a coordinate transformation processor that transforms a coordinate of the second candidate region to a coordinate of the first posture based on the deformation displacement field, an association processor that associates the first candidate region with the transformed second candidate region that is close to the first candidate region, and a same object determination processor that determines that the object candidates included in the candidate regions associated with each other by the association processor are the same object and are the specific object.

Supplementary Note 2

The object detection device according to Supplementary Note 1, further comprising a first object determination processor that determines that the object candidate included in the first candidate region is the specific object, and a second object determination processor that determines that the object candidate included in the second candidate region is the specific object.

Supplementary Note 3

The object detection device according to Supplementary Note 2, in which the first object determination processor determines that the object candidate included in the first candidate region is the specific object, and the second object determination processor determines that the object candidate included in the second candidate region is the specific object.

Supplementary Note 4

The object detection device according to Supplementary Note 3, in which the same object determination processor generates a main score indicating certainty that the object candidates included in the candidate regions are the same object and are the specific object, the first object determination processor generates a first sub-score indicating certainty that the object candidate included in the first candidate region is the specific object, and the second object determination processor generates a second sub-score indicating certainty that the object candidate included in the second candidate region is the specific object.

Supplementary Note 5

The object detection device according to Supplementary Note 4, further comprising a detection processor that detects, as the specific object, an object candidate having the main score equal to or greater than a first threshold value, an object candidate having the first sub-score equal to or greater than a second threshold value, which is greater than the first threshold value, and an object candidate having the second sub-score equal to or greater than the second threshold value.

In the technology of the present disclosure, it is also possible to appropriately combine the embodiment described above with various modification examples. In addition, it is needless to say that the technology of the present disclosure is not limited to the embodiment described above and the modification example, and various configurations can be adopted without departing from the gist of the technology of the present disclosure. Further, the technology of the present disclosure includes, in addition to the program, a storage medium that stores the program in a non-transitory manner.

The description contents and the shown contents above are the detailed description of the parts according to the technology of the present disclosure, and are merely examples of the technology of the present disclosure. For example, the above descriptions of the configuration, the function, the action, and the effect are the descriptions of examples of the configuration, the function, the action, and the effect of the parts according to the technology of the present disclosure. Therefore, it is needless to say that unnecessary parts may be deleted, new elements may be added, or replacements may be made with respect to the description contents and the shown contents above within a range that does not deviate from the gist of the technology of the present disclosure. In addition, in order to avoid complications and facilitate understanding of the parts according to the technology of the present disclosure, in the description contents and the shown contents above, the description of common technical knowledge and the like that do not particularly require description for enabling the implementation of the technology of the present disclosure are omitted.

All documents, patent applications, and technical standards described in the present specification are incorporated into the present specification by reference to the same extent as in a case in which the individual documents, patent applications, and technical standards are specifically and individually stated to be incorporated by reference.

What is claimed is:

1. An object detection device that detects a specific object included in an input image, the device comprising:
a first candidate region specifying processor that specifies a first candidate region in which an object candidate is included from a first input image obtained by imaging a subject in a first posture;
a second candidate region specifying processor that specifies a second candidate region in which an object candidate is included from a second input image obtained by imaging the subject in a second posture different from the first posture;
a deformation displacement field generation processor that generates a deformation displacement field between the first input image and the second input image;
a coordinate transformation processor that transforms a coordinate of the second candidate region to a coordinate of the first posture based on the deformation displacement field;
an association processor that associates the first candidate region with the transformed second candidate region that is close to the first candidate region; and
a same object determination processor that determines that the object candidates included in the candidate regions associated with each other by the association processor are the same object and are the specific object,
wherein the same object determination processor generates a main score indicating certainty that the object candidates included in the candidate regions are the same object and are the specific object.

2. The object detection device according to claim 1, further comprising:
a first object determination processor that determines that the object candidate included in the first candidate region is the specific object; and
a second object determination processor that determines that the object candidate included in the second candidate region is the specific object.

3. The object detection device according to claim 2,
wherein the first object determination processor determines that the object candidate included in the first candidate region is the specific object, and
the second object determination processor determines that the object candidate included in the second candidate region is the specific object.

4. The object detection device according to claim 3, wherein
the first object determination processor generates a first sub-score indicating certainty that the object candidate included in the first candidate region is the specific object, and
the second object determination processor generates a second sub-score indicating certainty that the object candidate included in the second candidate region is the specific object.

5. The object detection device according to claim 4, further comprising:
a detection processor that detects, as the specific object, an object candidate having the main score equal to or greater than a first threshold value, an object candidate having the first sub-score equal to or greater than a second threshold value, which is greater than the first threshold value, and an object candidate having the second sub-score equal to or greater than the second threshold value.

6. The object detection device according to claim 2,
wherein the first object determination processor corrects the first candidate region, and
the second object determination processor corrects the second candidate region.

7. The object detection device according to claim 1, further comprising:
a first convolution neural network that generates a first convolution feature map from the first input image; and
a second convolution neural network that generates a second convolution feature map from the second input image,
wherein the first candidate region specifying processor specifies the first candidate region based on the first convolution feature map, and
the second candidate region specifying processor specifies the second candidate region based on the second convolution feature map.

8. The object detection device according to claim 7,
wherein the deformation displacement field generation processor is a convolution neural network that generates the deformation displacement field from the first convolution feature map and the second convolution feature map.

9. The object detection device according to claim 1,
wherein one of a supine position and a prone position is the first posture, and the other of the supine position and the prone position is the second posture.

10. The object detection device according to claim 1,
wherein the specific object is a polyp.

11. An object detection method of detecting a specific object included in an input image, the method comprising:
specifying a first candidate region in which an object candidate is included from a first input image obtained by imaging a subject in a first posture;
specifying a second candidate region in which an object candidate is included from a second input image obtained by imaging the subject in a second posture different from the first posture;
generating a deformation displacement field between the first input image and the second input image;
transforming a coordinate of the second candidate region to a coordinate of the first posture based on the deformation displacement field;
associating the first candidate region with the transformed second candidate region that is close to the first candidate region;
determining that the object candidates included in the candidate regions associated with each other are the same object and are the specific object; and
generating a main score indicating certainty that the object candidates included in the candidate regions are the same object and are the specific object.

12. A non-transitory computer-readable storage medium storing a program operating a computer as an object detection device that detects a specific object included in an input image, the program causing the computer to perform a process comprising:
specifying a first candidate region in which an object candidate is included from a first input image obtained by imaging a subject in a first posture;
specifying a second candidate region in which an object candidate is included from a second input image obtained by imaging the subject in a second posture different from the first posture;
generating a deformation displacement field between the first input image and the second input image;
transforming a coordinate of the second candidate region to a coordinate of the first posture based on the deformation displacement field;
associating the first candidate region with the transformed second candidate region that is close to the first candidate region;
determining that the object candidates included in the candidate regions associated with each other are the same object and are the specific object; and
generating a main score indicating certainty that the object candidates included in the candidate regions are the same object and are the specific object.

* * * * *